US008883089B2

(12) United States Patent
Grenz et al.

(10) Patent No.: US 8,883,089 B2
(45) Date of Patent: Nov. 11, 2014

(54) SAMPLE PREPARATION DEVICE AND METHOD UTILIZING POLYAMIDE TUBE

(75) Inventors: Robert Lee Grenz, Santa Ana, CA (US); William Christopher Hudson, Tustin, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 815 days.

(21) Appl. No.: 12/116,041

(22) Filed: May 6, 2008

(65) Prior Publication Data

US 2008/0277347 A1 Nov. 13, 2008

Related U.S. Application Data

(60) Provisional application No. 60/928,235, filed on May 8, 2007.

(51) Int. Cl.
| | | |
|---|---|---|
| *G01N 33/00* | (2006.01) | |
| *B01D 15/00* | (2006.01) | |
| *B01L 3/00* | (2006.01) | |
| *G01N 1/40* | (2006.01) | |
| *B01D 15/22* | (2006.01) | |
| *B01D 15/18* | (2006.01) | |
| *G01N 30/00* | (2006.01) | |
| *G01N 30/60* | (2006.01) | |

(52) U.S. Cl.
CPC ............ *G01N 30/6901* (2013.01); *B01D 15/22* (2013.01); *B01L 2300/0681* (2013.01); *B01L 2300/0829* (2013.01); *B01D 15/1885* (2013.01); *B01L 2200/142* (2013.01); *G01N 2030/009* (2013.01); *B01L 3/50255* (2013.01); *B01L 2200/0631* (2013.01); *G01N 30/6043* (2013.01); *G01N 1/40* (2013.01)
USPC .......................................... 422/500; 422/50

(58) Field of Classification Search
CPC ................................. G01N 33/00; B01D 15/00
USPC ............................. 402/102; 422/102, 500, 50
See application file for complete search history.

(56) References Cited

U.S. PATENT DOCUMENTS

| | | | | |
|---|---|---|---|---|
| 4,277,259 | A | | 7/1981 | Rounbehler et al. |
| 4,871,675 | A | * | 10/1989 | Coupek et al. ............. 435/307.1 |
| 5,037,544 | A | * | 8/1991 | Snyder ........................ 210/198.2 |
| 5,114,658 | A | * | 5/1992 | Katsaros ....................... 264/537 |
| 6,451,260 | B1 | | 9/2002 | Dusterhoft et al. |

(Continued)

FOREIGN PATENT DOCUMENTS

| | | |
|---|---|---|
| EP | 0875271 A | 11/1998 |
| EP | 0875271 A2 | 11/1998 |

(Continued)

OTHER PUBLICATIONS

Symco Hylon Nylon 6/6 N1213HL (Dry Economy Grade). Copyright Date 2004. Two pages.*

(Continued)

*Primary Examiner* — Christine T Mui

(57) ABSTRACT

Polyamide sample preparation tubes with a hollow polyamide tube and an extraction medium contained within the tube are utilized in the sample preparation devices. The sample preparation tubes are substantially inert and show little tendency to dissolve or leach contaminants into non-aqueous liquids. The polyamide tubes may be used in preparing samples for analytical procedures such as GC, GC/MS, LC or LC/MS.

16 Claims, 6 Drawing Sheets

(56) References Cited

U.S. PATENT DOCUMENTS

| | | |
|---|---|---|
| 6,613,560 B1 | 9/2003 | Tso et al. |
| 7,060,192 B2 | 6/2006 | Yuzhakov et al. |
| 2005/0082213 A1 | 4/2005 | DeMarco |
| 2006/0039827 A1 | 2/2006 | Zhang et al. |
| 2006/0198765 A1* | 9/2006 | Gjerde et al. ............ 422/102 |
| 2007/0036685 A1* | 2/2007 | Bakry et al. ............ 422/101 |

FOREIGN PATENT DOCUMENTS

| | | |
|---|---|---|
| GB | 2017911 A | 10/1979 |
| JP | 61165634 | 7/1986 |
| JP | 1035363 A | 2/1989 |
| JP | 6435363 | 2/1989 |
| JP | 0212057 | 1/1990 |
| JP | 2007503595 | 12/2004 |
| JP | 2003254877 | 8/2012 |
| WO | 8809201 | 12/1988 |
| WO | WO 88/09201 A | 12/1988 |
| WO | WO 2004079005 A1 * | 9/2004 ............ C12Q 1/68 |
| WO | 2004106914 A1 | 12/2004 |

OTHER PUBLICATIONS

Beall, Glenn; "Designing With Nylon (Part 1)"; IDES Website; retrieved from http://www.ides.com/articles/design/2006/beall02.asp; retrieved on Jul. 5, 2011, pp. 1-2.

Anonymous; Tech Notes, Moisture Conditioning of VYDYNE Polyamide 66 Resins, retrieved from http://www.vydyne.co.kr/aplus_data/productitechnL2/3.Moisture%20conditioning%20of%20nylon.pdf; retrieved on Jul. 5, 2011, pp. 1-3.

* cited by examiner

SAMPLE PREPARATION DEVICE AND METHOD UTILIZING POLYAMIDE TUBE

This application claims priority from provisional application Ser. No. 60/928,235 filed May 8, 2007.

FIELD OF THE INVENTION

This invention relates generally to devices and methods for preparing samples and, more particularly, to polyamide tubes and methods of their use in sample preparation.

BACKGROUND OF THE INVENTION

Sample preparation is an essential stage in many analytical processes. Preparation procedures may involve, for example, removal of undesired components present in the sample, exchanging one solvent in which an analyte is dissolved for another solvent or concentrate an analyte among other things. Solid Phase Extraction ("SPE") is one such sample preparation procedure that may be used for sample extraction, concentration and cleanup. Typical SPE devices utilize packed beds of sorbent contained between porous filter discs within a SPE tube.

When nonaqueous liquids are used in SPE processes, it is generally desirable that the tubes be constructed of a material that will not dissolve or leach contaminants into the nonaqueous liquid. Ultra-clean polypropylene has been traditionally used, however, the inventors show herein that when using a nonaqueous liquids, contaminants are dissolved or leached from polypropylene SPE tubes and from high density polyethylene SPE tubes as well. Thus, there is a need for SPE tubes that are substantially inert and do not dissolve or leach contaminants into nonaqueous liquids.

SUMMARY

Accordingly, the inventors have succeeded in devising novel sample preparation tubes that are substantially inert to nonaqueous liquids in comparison to the traditional polypropylene tubes. The new sample preparation tubes are constructed of polyamide and, particularly, nylon, which confers the chemical inertness on the tubes.

Thus, in one example of an implementation, a sample preparation device is provided. The device includes a hollow polyamide tube, in particular, a nylon tube and an extraction medium contained within the tube. The polyamide tube has both an inlet and an outlet and, in various implementations, the extraction medium may be contained between an inlet-side fritted glass filter and an outlet-side fritted glass filter, which are also contained within the tube. In addition, the tube may further contain a polyamide screen between the inlet-side fritted glass filter and the tube inlet.

In another example of an implementation, a method of making a device for sample preparation such as is described above is provided. The method includes providing a hollow polyamide tube, in particular, a nylon tube and placing an extraction medium within the tube. In certain implementations, the extraction medium is placed between an inlet-side and an outlet-side fritted glass filter, which are also within the tube. In addition, a polyamide screen may be placed between the inlet-side fritted glass filter and the tube inlet.

Another example of an implementation provides a method for preparing a sample using a device as described above. The method may include (a) providing a hollow polyamide tube, in particular, a nylon tube containing an extraction medium; (b) conditioning the extraction medium; (c) directing the sample through the conditioned extraction medium to retain sample impurities; and (d) collecting the prepared sample emerging from the extraction medium.

In a further example of an implementation, a method is provided for preparing a sample to be analyzed using a sample preparation device. The method includes (a) providing a hollow polyamide tube, in particular a nylon tube, containing an extraction medium; (b) conditioning the extraction medium; (c) adsorbing one or more analytes present in the sample to be analyzed to the conditioned extraction medium; and (d) eluting the one or more adsorbed analytes from the extraction medium.

Other devices, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

The invention can be better understood with reference to the following figures. The components in the figures are not necessarily to scale, emphasis instead being placed upon illustrating the principles of the invention.

DETAILED DESCRIPTION OF THE INVENTION

Figure 1:
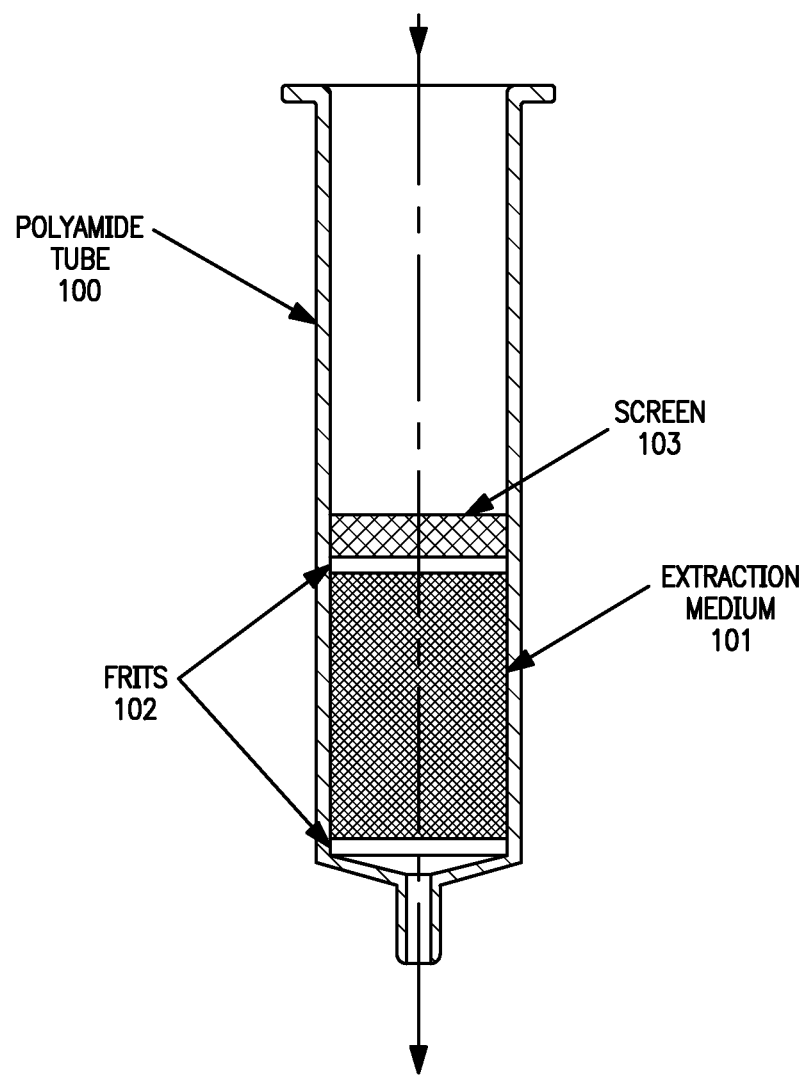
FIG. 1 illustrates one implementation of a polyamide sample preparation device.

The present invention is directed to polyamide sample preparation tubes. The tubes are substantially inert in comparison to traditional polypropylene tubes. The chemical inert quality of the new tubes results from their polyamide composition. Polyamide or nylon has not traditionally been considered for making sample preparation tubes and, in particular, SPE tubes. This is because it has generally been thought that traditional polypropylene tubes are sufficiently clean for the procedures performed. However, new tests have been introduced requiring cleaner extracts. Whereas tubes made of TEFLON® and other fluorinated polymers have been considered, nylon has not heretofore been considered as a possible material for making SPE tubes that have a level of inertness sufficient for the newer tests.

The term polyamide as used herein is intended to refer to polymers joined by peptide bonds and, in particular, to nylon polymers. The nylon polymers of the present invention are thermoplastics such as those formed by reaction of diamine and dicarboxylic acid polymers. For example, nylon 6/6 can be formed by reaction of hexamethylene diamine with adipic acid. Other nylon polymers can be prepared by different preparative methods known in the art. For example, the homopolymer nylon 6 can be formed by a ring-opening polymerization of caprolactam or by polymerizing aminocaproic acid. Any of a variety of nylon polymers may be used for the sample preparation tubes of the present invention so long as the nylon polymer can be formed into a hollow tube suitable for containing the extraction medium and for mounting and use in an extraction procedure. By way of a non-limiting example, some of the members of the nylon family that may be used in the present invention include nylon 11; nylon 12; nylon 12/12; nylon 4/6; nylon 6; nylon 6/10; nylon 6/12; nylon 6/6 and nylon 6/9. It is also possible to use combinations of the above nylons.

Thus, in various implementations, the polyamides of the invention may be synthetic polyamides; in various implementations the polyamides may be nylons; in various implementations, the polyamides may be homo-polymers or co-polymers; and in various implementations the polyamides may be a mixture of polyamides or a combination of one or more polyamides with one or more other polymers.

The polyamide tubes may be made, for example, by an injection molding process. Typically, the nylon 6/6 polymer may be first dried to a moisture content of less than 0.2%. The polymer may then be melted, e.g. at a temperature from about 500° to about 600° F. and injected into a relatively cool metal mold under high pressure, e.g. from about 10,000 to about 18,000 psi. The polymer may then be allowed to solidify under pressure and the nylon tube removed.

Injection molds designed for polypropylene are not readily adaptable to making nylon SPE tubes. The gates are on the small side along with the runners and these feed the material from the press to the cavities. Because of the stiffness of nylon, the puller pins, which strip out the runners from the cavity, need to be undercut more so than is required for injection molding of polypropylene. One variation in the method is that there be more draft (angle) on the core pins to eliminate the pulling of the nozzle end of the tube.

The terms "sample preparation tube", "sample preparation device" and "sample preparation column" are intended to be used interchangeably herein in reference to the present invention.

The sample preparation device includes within the hollow polyamide tube, an extraction medium. The extraction medium may be a non-polar, mixed-mode or ion exchange sorbent. By way of non-limiting examples only, non-polar sorbents may include functionalized silica based sorbent such as an octadecyl functionalized silica or resin based sorbent such as a styrene divinyl benzene polymer; mixed-mode sorbents may include silica based sorbents with a bonded functional group such as sulfonic acid and quaternary amine; and ion exchange sorbents may include silica based sorbents with an anionic exchanger such as an amino propyl group or cationic exchanger such as a carboxylic acid group or a propyl-sulfonic acid group. Thus, a wide range of sorbents may thus be used in the sample preparation tubes of the invention and the range of sorbents that may be used is not intended to be limited to any particular sorbent or class of sorbent.

The sample preparation tubes of the present invention may consist essentially of a hollow polyamide tube containing an extraction medium, which may be selected for the particular sample type and preparation desired. Other components may also be present and an example of a polyamide tube, extraction medium and other components is illustrated in one implementation of the sample preparation tubes as shown in FIG. 1.

FIG. 1 illustrates a sample preparation tube 1 that includes a hollow polyamide tube 100 as shown. In the example shown in the figure, the inlet side of the polyamide tube is shown at the top and the outlet side of the polyamide tube is shown at the bottom with the direction of flow of sample and solvent being indicated by arrows. In the implementation shown in the figure, the outlet side has a smaller diameter than the inlet side. As shown in the figure, an extraction medium 101 is contained between an inlet-side and outlet-side frits 102, which may be fritted glass filters. The smaller diameter of the outlet side may serve to maintain the component within the polyamide tube. In addition, the tube may further contain a polyamide screen 103 between the inlet-side fritted glass filter and the tube inlet and this screen 103 can serve to hold the parts in place within the tube.

Figure 2:
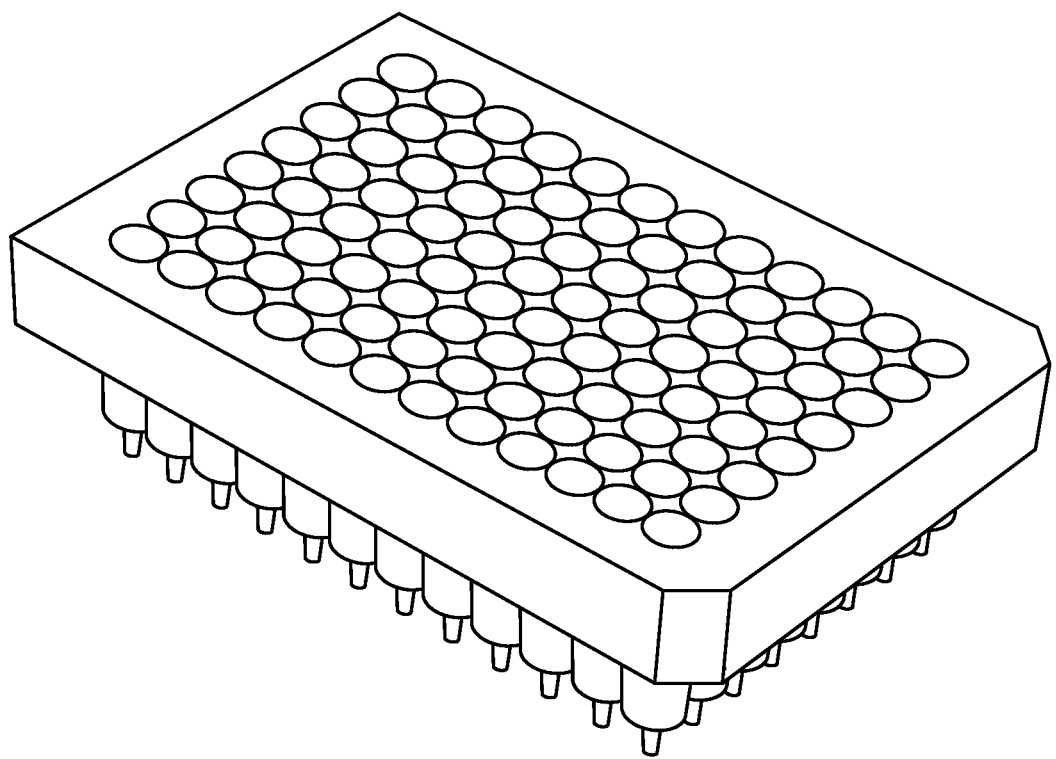
FIG. 2 illustrates a 96-well plate format for the polyamide sample preparation devices of FIG. 1.

The polyamide sample preparation tubes may be of any suitable size, shape or extraction medium composition such as that described U.S. Patent Application Publication No. 2006/0216206. Further, the size of the polyamide sample preparation tubes may be suitable for samples in the microliter range such as 20, 25, 50, 100, 200, 500 microliter and the like or in the mL range such as, for example 1, 3, 6, 12, 20, 60, 140 mL and the like. In addition, the polyamide sample preparation tubes may be assembled into well plate formats such as, for example one or two mL 96 well plate format as illustrated in FIG. 2. Other well plate formats may be used having 6, 24, 96, 384, 1536 or more sample preparation tubes arranged in a 2:3 rectangular matrix and in microliter or mL sizes as described above.

The polyamide sample preparation tubes may be used for solid phase extraction, protein filtering or sample cleanup. In particular, the polyamide sample preparation tubes may be used for sample preparation prior to analysis in conjunction with such analytical methods as GC, GC/MS, LC, LC/MS and the like.

The polyamide preparation tubes are relatively inert and show little tendency to dissolve or leach contaminants into nonaqueous liquids. The inertness of the polyamide preparation tubes is illustrated in the example below.

EXAMPLE

This example illustrates the relative inertness of polyamide sample preparation tubes to dichloromethane in comparison to that of sample preparation tubes made of polypropylene, high density polyethylene and TEFLON®.

Polyamide sample preparation tubes were prepared using nylon 6/6 in an injection molding procedure. The nylon 6/6 was first dried to a moisture content of less than 0.2%. The polymer was then melted and injected into a cool metal mold under pressure.

Figure 3:
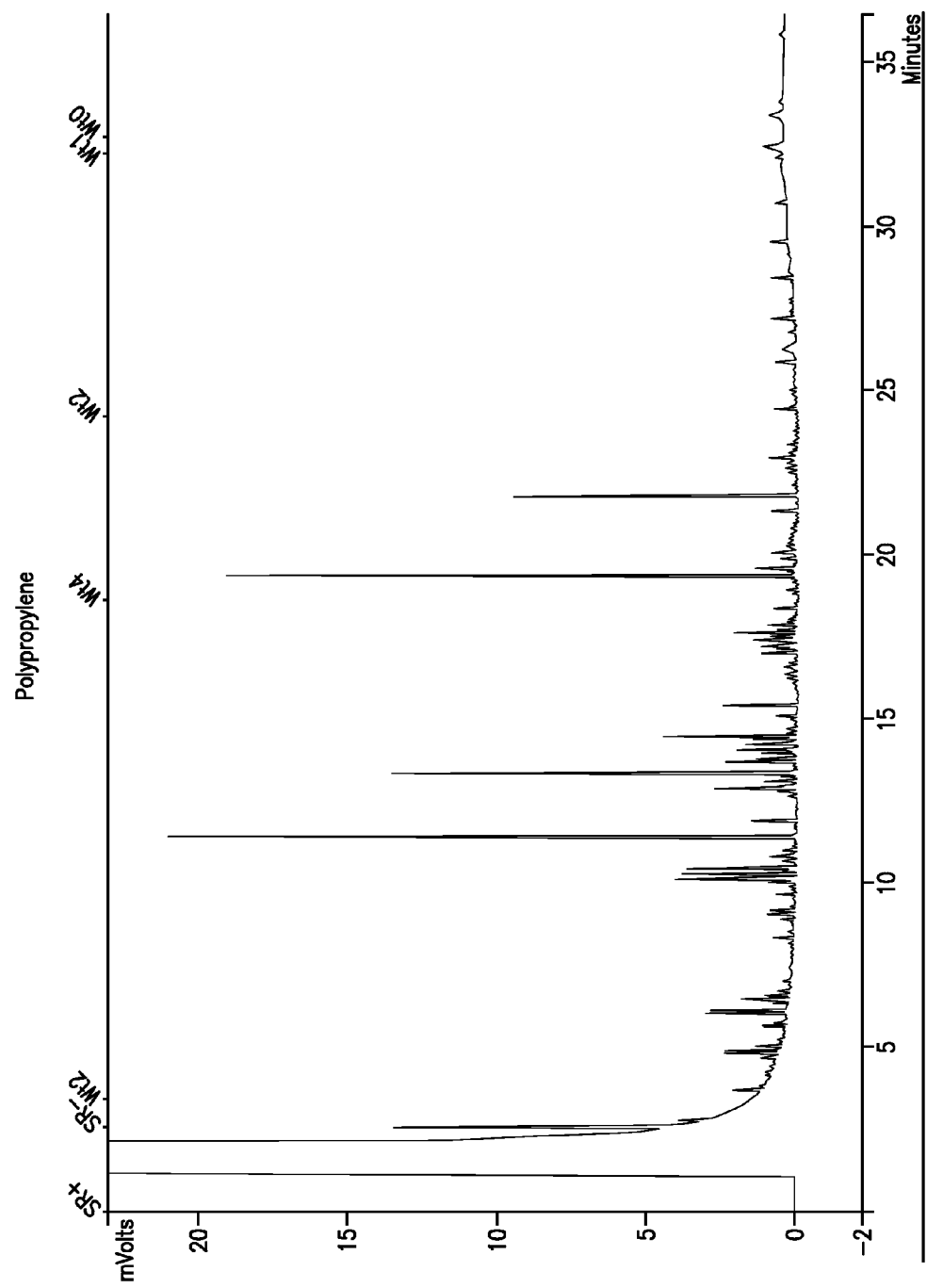
FIG. 3 illustrates a GC/FID chromatogram of dichloromethane passed through a polypropylene SPE tube.
Figure 4:
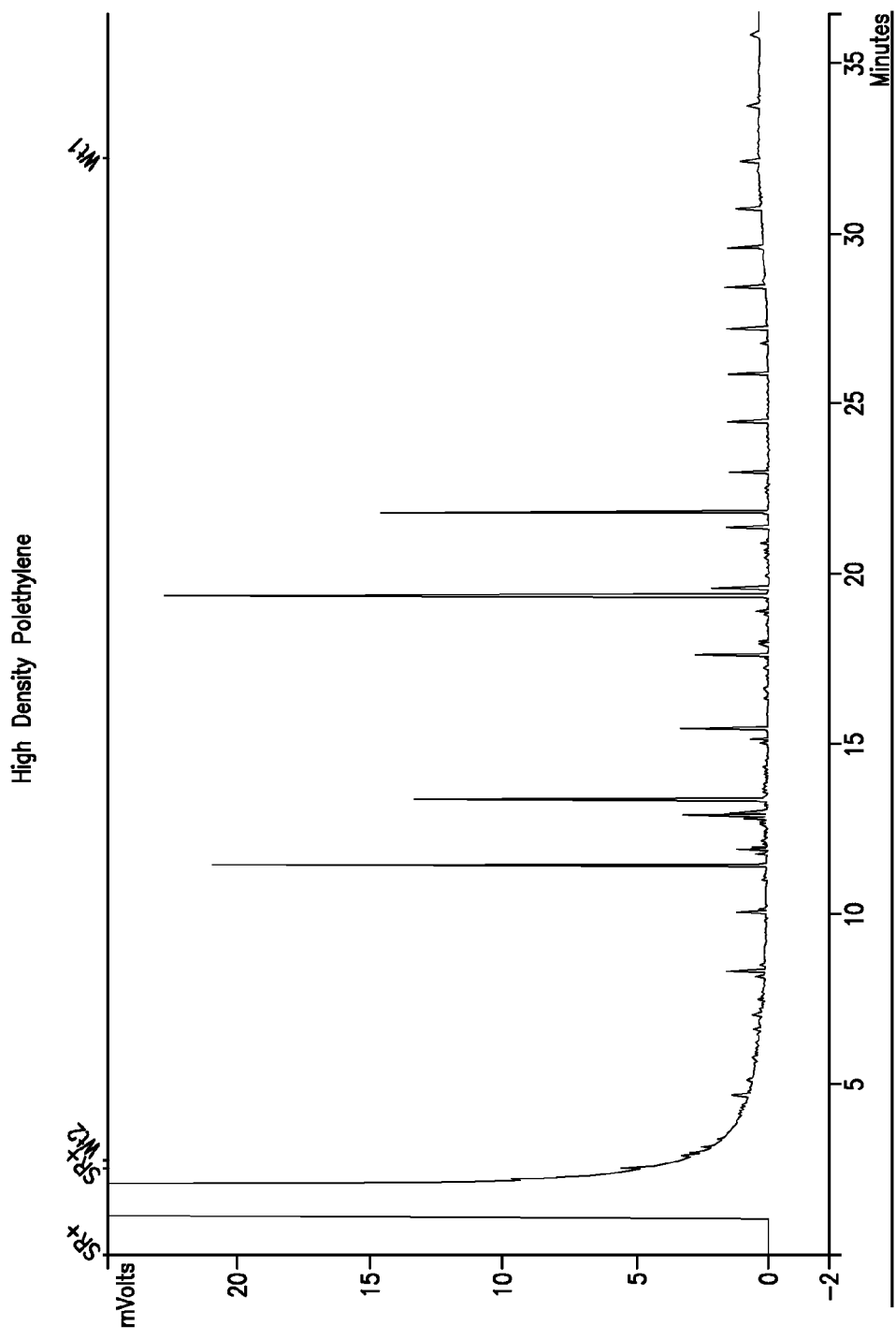
FIG. 4 illustrates a GC/FID chromatogram of dichloromethane passed through a high density polyethylene SPE tube.
Figure 5:
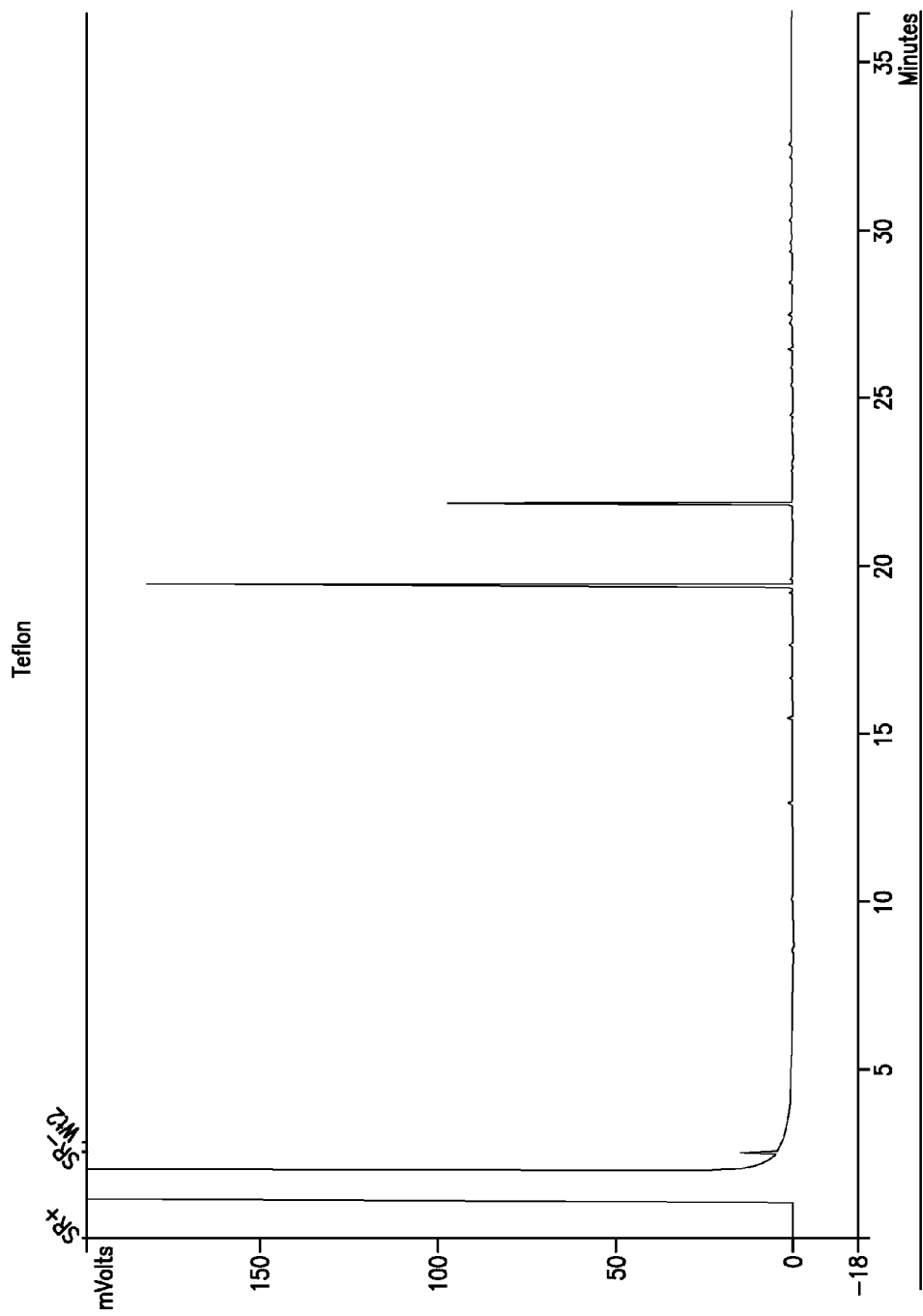
FIG. 5 illustrates a GC/FID chromatogram of dichloromethane passed through a TEFLON® SPE tube.
Figure 6:
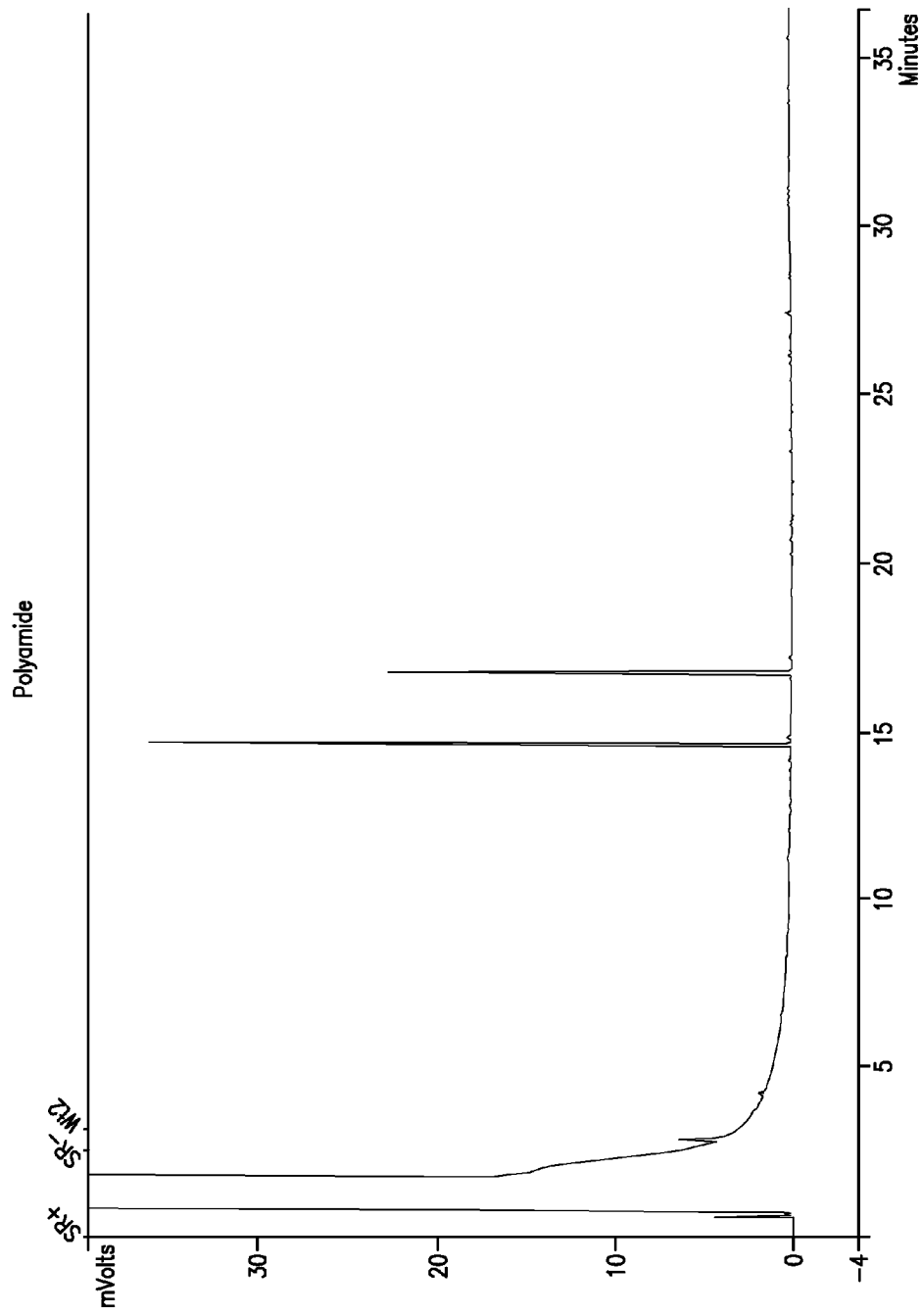
FIG. 6 illustrates a GC/FID chromatogram of dichloromethane passed through a polyamide SPE tube according to an implementation of the invention.

Dichloromethane was passed through the polyamide sample preparation tube and analyzed using GC/FID. The chromatogram thus produced was then compared to that obtained upon passing dichloromethane through tubes composed of polypropylene, high density polyethylene and TEFLON® using GC/FID analysis. As shown in the chromatograms in FIGS. 3 and 4, contaminants are present in the effluent from both polypropylene and high density polyethylene tubes. In comparison to this, the effluent from the polyamide tube was substantially free of contaminants as shown in FIG. 6 and better to that obtained with the TEFLON® tube as shown in FIG. 5.

While various embodiments of the invention have been described, it will be apparent to those of ordinary skill in the art that many more embodiments and implementations are possible within the scope of this invention. Accordingly, the invention is not to be restricted except in light of the attached claims and their equivalents.

Although there has been hereinabove described a specific sample preparation device and method utilizing polyamide tube in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A sample preparation device comprising:
   a hollow polyamide tube formed from nylon 6/6 with a moisture content of less than 0.2%, the tube comprising an inlet, an outlet, and an inside surface extending from the inlet to the outlet, wherein the tube is formed without an additional layer on the inside surface such that the inside surface is exposed to and defines the interior;
   an inlet-side fritted glass filter and an outlet-side fitted glass filter, both filters being contained within the tube; and
   an extraction medium filling a portion of the interior between said inlet-side fitted glass filter and said outlet-side fritted glass filter.

2. The sample preparation device of claim 1, further comprising a polyamide screen between the inlet-side fritted glass filter and the inlet, wherein said outlet has a smaller diameter than said inlet.

3. The sample preparation device of claim 1, wherein said nylon tube has the chemical inert quality properties shown in FIG. 6 when used in an extraction process wherein the sample is dissolved or eluted with a nonaqueous solvent.

4. The sample preparation device of claim 1, wherein said extraction medium is selected from the group consisting of functionalized silica based sorbents, resin based sorbents, mixed-mode sorbents and ion exchange sorbents.

5. The sample preparation device of claim 3, wherein said extraction medium is selected from the group consisting of octadecyl functionalized silica, styrene divinyl benzene polymer, silica based sorbent with a bonded functional group such as sulfonic acid and quaternary amine and silica based sorbents with an anionic exchanger such as an amino propyl group or cationic exchanger such as a carboxylic acid group or a propylsulfonic acid group.

6. A well plate format comprising a multiplicity of sample preparation devices of claim 1, each sample preparation device further comprising:
   a polyamide screen between the inlet-side fritted glass filter and the inlet, wherein said polyamide of said polyamide screen is nylon.

7. The well plate format of claim 6, being a 96 well plate format.

8. A method of making a device for sample preparation comprising:
   providing a hollow polyamide tube formed from nylon 6/6 with a moisture content of less than 0.2%, the tube comprising an inlet, an outlet, and an inside surface extending from the inlet to the outlet, wherein the tube is formed without an addition layer on the inside surface such that the inside surface is exposed to and defines the interior;
   placing an inlet-side fritted glass filter and an outlet-side fitted glass filter within said tube; and
   filling in an extraction medium into the tube between said inlet-side and said outlet-side fritted glass filter.

9. The method of claim 8, wherein said nylon tube has the chemical inert quality properties shown in FIG. 6 when used in an extraction process, wherein the sample is dissolved or eluted with a nonaqueous solvent.

10. The method of claim 8, wherein said extraction medium is selected from the group consisting of functionalized silica based sorbents, resin based sorbents, mixed-mode sorbents and ion exchange sorbents.

11. The method of claim 9, wherein said extraction medium is selected from the group consisting of octadecyl functionalized silica, styrene divinyl benzene polymer, silica based sorbent with a bonded functional group such as sulfonic acid and quaternary amine and silica based sorbents with an anionic exchanger such as an amino propyl group or cationic exchanger such as a carboxylic acid group or a propylsulfonic acid group.

12. The method of claim 8, wherein said polyamide tube is made by an injection molding process which comprises drying a nylon polymer to a moisture content of less than 0.2%, melting said dried polymer at a temperature from about 500° to about 600° F., injecting said heated polymer into a relatively cool metal mold under high pressure of from about 10,000 to about 18,000 psi., allowing the polymer to solidify under pressure and removing said polyamide tube.

13. A method for preparing a sample using a device according to claim 1, comprising:
   providing the device of claim 1;
   conditioning the extraction medium;
   directing a sample through the conditioned extraction medium;
   adsorbing one or more analytes present in the sample to be analyzed to the conditioned extraction medium; and
   eluting at least one of said adsorbed analytes from the extraction medium.

14. The method of claim 13, further comprising placing a polyamide screen between the inlet-side fritted glass filter and the tube inlet.

15. The method of claim 13, wherein said sample is eluted with a nonaqueous solvent.

16. A sample preparation device comprising:
   a hollow polyamide tube formed from nylon, the tube comprising an inlet, an outlet, and an inside surface extending from the inlet to the outlet, wherein the tube is formed without an additional layer on the inside surface such that the inside surface is exposed to and defines the interior;
   an inlet-side fritted glass filter and an outlet-side fitted glass filter, both filters being contained within the tube;
   an extraction medium filling a portion of the interior between said inlet-side fitted glass filter and said outlet-side fitted glass filter; and
   a polyamide screen between the inlet-side fritted glass filter and the inlet, wherein said outlet has a smaller diameter than said inlet,
   wherein the nylon is selected from the group consisting of nylon 11, nylon 12, nylon 12/12, nylon 4/6, nylon 6, nylon 6/10, nylon 6/12, nylon 6/6, nylon 6/9 and combinations thereof.

* * * * *

UNITED STATES PATENT AND TRADEMARK OFFICE
CERTIFICATE OF CORRECTION

PATENT NO. : 8,883,089 B2
APPLICATION NO. : 12/116041
DATED : November 11, 2014
INVENTOR(S) : Robert Lee Grenz et al.

It is certified that error appears in the above-identified patent and that said Letters Patent is hereby corrected as shown below:

In the Claims,

In column 5, line 21, In Claim 1, delete "fitted" and insert -- fritted --, therefor.

In column 5, line 25, In Claim 1, delete "fitted" and insert -- fritted --, therefor.

In column 5, line 28, In Claim 2, delete "fitted" and insert -- fritted --, therefor.

In column 6, line 2, In Claim 8, delete "fitted" and insert -- fritted --, therefor.

In column 6, line 50, In Claim 16, delete "fitted" and insert -- fritted --, therefor.

In column 6, line 53, In Claim 16, delete "fitted" and insert -- fritted --, therefor.

In column 6, line 54, In Claim 16, delete "fitted" and insert -- fritted --, therefor.

In column 6, line 55, In Claim 16, delete "fitted" and insert -- fritted --, therefor.

Signed and Sealed this
Seventeenth Day of February, 2015

Michelle K. Lee
*Deputy Director of the United States Patent and Trademark Office*